US006949354B2

(12) United States Patent
Villa et al.

(10) Patent No.: US 6,949,354 B2
(45) Date of Patent: Sep. 27, 2005

(54) METHODS FOR SCREENING COMPOUNDS ACTIVE ON NEURONS

(75) Inventors: Pascal Villa, Cassis (FR); Michel Delaage, Marseilles (FR); Toni Williamson, Cassis (FR); Christopher Henderson, Cassis (FR)

(73) Assignee: Trophos, Marseille Cedex (FR)

(*) Notice: Subject to any disclaimer, the term of this patent is extended or adjusted under 35 U.S.C. 154(b) by 114 days.

(21) Appl. No.: 10/149,114

(22) PCT Filed: Dec. 7, 2000

(86) PCT No.: PCT/EP00/12340

§ 371 (c)(1),
(2), (4) Date: Jul. 12, 2002

(87) PCT Pub. No.: WO01/42784

PCT Pub. Date: Jun. 14, 2001

(65) Prior Publication Data

US 2003/0077665 A1 Apr. 24, 2003

(30) Foreign Application Priority Data

Dec. 9, 1999 (EP) .............................. 99403092

(51) Int. Cl.⁷ .............................. C12Q 1/00; C12Q 1/02; C12N 5/06; A01K 67/027
(52) U.S. Cl. ............................. 435/29; 435/4; 435/325; 800/8
(58) Field of Search ............................. 435/4, 29, 325; 800/8

(56) References Cited

U.S. PATENT DOCUMENTS 5,902,732 A    5/1999  Hochman ................. 73/701
6,060,247 A  * 5/2000  Miller et al. ................ 435/6

FOREIGN PATENT DOCUMENTS

| WO | 96/30541 A | 10/1996 |
| WO | 96/40982 A | 12/1996 |
| WO | 99/10741 A | 3/1999 |
| WO | WO 99/10741 A2 * | 3/1999 |
| WO | 99/11758 A | 3/1999 |

OTHER PUBLICATIONS

U.S. Appl. No. 60/031,057, <<copy not readily available>>.*
Galter et al. Regulation of the transmitter phenotype of rostral and caudal groups of cultured serotonergic raphe neurons. Neuroscience. Jan. 1999;88(2):549–59.*
Hanani M. Neurons and glial cells of the enteric nervous system: studies in tissue culture. J Basic Clin Physiol Pharmacol. Jul.–Sep. 1993;4(3):157–79.*
Honegger et al. Muscimol–induced death of GABAergic neurons in rat brain aggregating cell cultures. Brain Res Dev Brain Res. Feb. 10, 1998;105(2):219–25.*
Kenny et al. The application of high–throughput screening to novel lead discovery. Prog Drug Res. 1998;51:245–69.*
Kew et al. Neuroscience. Feb. 1997;76(3):809–20.*
Oberpichler–Schwenk et al. Primary cultures of neurons for testing neuroprotective drug effects. J Neural Transm Suppl. 1994;44:1–20.*
Pellegrini et al. Delayed administration of memantine prevents N–methyl–D–aspartate receptor–mediated neurotoxicity. Ann Neurol. Apr. 1993;33(4):403–7.*
Yan et al. Cultured cerebellar granule neurons as a model of neuronal apoptosis. Neuromethods 1997; 29:47–66.*
Mattson et al; "Isolated Hippocampal Neurons in Cryopreserved Long Term Cultures: Development of Neuroarchitecture and Sensitivity to NMDA"; International Journal of Developmental Neuroscience, vol. 6, No. 5, pp. 439–452, XP000904823.
Bekkers et al; "Exitatory and Inhibitory Autaptic Currents in Isolated Hippocampal Neurons Maintained in Cell Culture", Proceedings of the National Academy of Sciences of USA, vol. 88, No. 17, Sep. 1991, pp. 7834–7838, XP000891942.
Van De Pol et al; "NILE/L1 and NCAM–Polysialic Acid Expression on Growing Axons of Isolated Neurons", Journal of Comparative Neurology, vol. 332, No. 2, Jun. 8, 1993, pp. 237–257, XP000904943.

* cited by examiner

*Primary Examiner*—David Guzo
*Assistant Examiner*—Daniel M. Sullivan
(74) *Attorney, Agent, or Firm*—Nixon & Vanderhye P.C.

(57) ABSTRACT

The present invention relates to compositions and methods for screening and/or identifying compounds exhibiting biological activity on neurons. The invention also relates to the isolation and culture of neurons, methods of inducing pathological conditions to said isolated neurons, as well as kits for implementing said methods. The invention can be used in experimental research, drug discovery, drug development, and the like. More particularly, the invention can be used to identify and/or characterize and/or improve compounds which are active on neurons and can be used for treating disorders of the nervous system.

12 Claims, 3 Drawing Sheets

METHODS FOR SCREENING COMPOUNDS ACTIVE ON NEURONS

Figure 1:
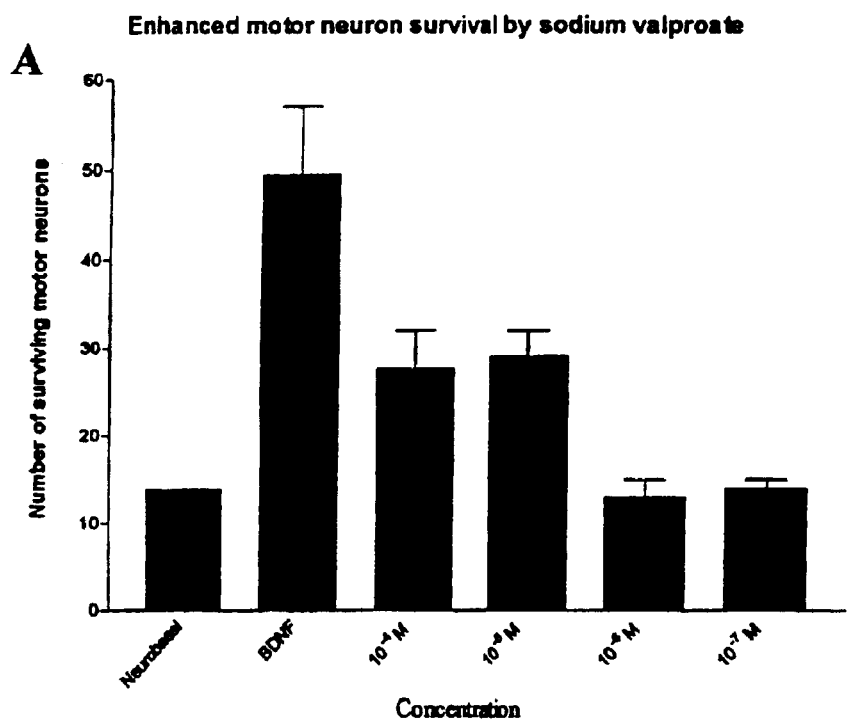
Figure 1:
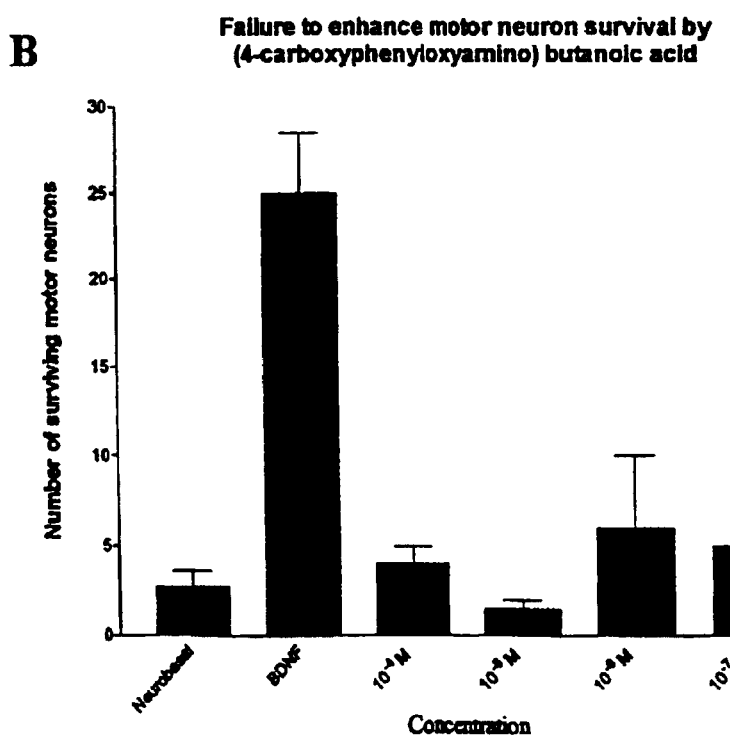

This application is the US national phase of international application PCT/EP00/12340 filed 7 Dec. 2000, which designated the US.

The present invention relates to compositions and methods for screening and/or identifying compounds exhibiting biological activity on neurons. The invention also relates to the isolation and culture of neurons, methods of inducing pathological conditions to said isolated neurons, as well as kits for implementing said methods. The invention can be used in experimental research, drug discovery, drug development, and the like. More particularly, the invention can be used to identify and/or characterize and/or improve compounds which are active on neurons and can be used for treating disorders of the nervous system.

There is a huge need for new drugs for neuro-degenerative diseases, especially in motor neuron diseases, Alzheimer's disease and Parkinson's disease. In spite of active chemical research, there are very few drug treatments available for these diseases and all of these are far from satisfactory.

Several methods have been reported in the art in order to identify compounds active on neuro-degenerative disorders. In particular, several recombinant cell lines expressing selected receptors involved in nervous transmission have been prepared and used to screen ligands thereof. However, these screening methods using isolated receptors have not led to useful, active compounds so far. This is probably because the appropriate targets have not been used. Other methods involve the screening of compounds inhibiting the production of therapeutic forms of proteins, such as beta amyloid peptide production. However, these methods only provide limited information regarding the candidate compounds, since they use artificial cellular systems which do not take into account the complexity of the nervous system. Standard mixed neuronal cultures are also not useful for testing compounds, because of the inability to follow the specific neurons of interest and to interpret cell interactions in terms of relevance to the pathological situation. Finally, it is not feasible to carry out animal testing, which is time-consuming, expensive, and not suitable to test the large number of compounds that come from combinatorial chemistry. Several screening assays or methods have been proposed, using poorly defined and/or specific cell populations, particular inducing conditions and a global signal detection (i.e., on the treated cell population as a whole), as described for instance in WO99/10741, WO96/40982).

The current invention now proposes and allows, for the first time, screening methods based on defined cell populations, at preferably low cell density cultures, and using an individualized read out, providing an increased sensitivity, reliability and a higher throughput.

The current invention now provides methods and compositions for testing compounds with biological activity on neurons. The invention can be performed with large numbers of candidate compounds, is sensitive and reproducible. The methods are also highly predictive since whole neurons are being used, which mimic the in vivo condition.

More specifically, the Applicant has uncovered that purified neurons, specific to a particular disease, can be isolated and cultured in sufficient quantity and reproducibility to be used in high throughput screening. Applicant has further shown that said isolated purified neurons can be handled by robots and cultured in microtiter plates of various sizes, at very low density (e.g., 25 neurons per $mm^2$ or less, particularly 10 neurons per $mm^2$ or less) so that a single neuron preparation can yield up to 10 000 microtiter wells or more, suitable for high throughput screening of compounds. Applicant has also shown that said isolated purified neurons in culture can be induced to die, mimicking a pathological process, in the presence or absence of one or several test compounds and that the death or survival of neurons can be monitored at the individual cell level (i.e., by analysing each or some of the isolated neurons, individually), in particular by fluorescence microscopy adapted to microtiter wells. The invention therefore represents a useful and predictive test for active compounds and to screen even large libraries of compounds.

A first object of the current invention thus resides in a method of identifying compounds active on neuronal cell function, comprising contacting a candidate compound in vitro with an isolated neuronal cell population and determining the effect of said candidate compound on the function of said cells.

Another object of the present invention lies in a method of identifying, selecting or characterizing a compound active on neuronal cell function, comprising contacting one or several candidate compounds in parallel with at least two different isolated neuronal cell populations, and determining the effect of said candidate compounds on the function of said cells.

A further object of this invention resides in a method of screening a library of compounds, comprising testing each or some compounds of the library for their activity on one or several isolated neuronal cell populations.

The invention also concerns isolated populations of specific neurons, high throughput methods of screening neuro-active compounds, methods of profiling neuro-active compounds, or methods of improving neuro-active compounds.

Within the context of the present invention, the term "compound" designates any product in isolated form or in mixture with any other material (e.g., any other product(s)). The compound may be defined in terms of structure and composition, or it may be undefined. For instance, the compound may be an isolated and structurally-defined product, an isolated product of unknown structure, a mixture of several known and characterized products or an undefined composition comprising one or several products. Examples of such undefined compositions include for instance tissue samples, biological fluids, cell supernatants, vegetal preparations, etc. The candidate compound may be any organic or inorganic product, including a polypeptide (or a protein or peptide), a nucleic acid, a lipid, a polysaccharide, a chemical product, or any mixture or derivatives thereof. The compounds may be of natural origin, synthetic origin, including libraries of compounds.

As will be further discussed below, the current invention is particularly adapted for the screening of large numbers of compounds, such as combinatorial libraries of compounds. Indeed, the instant invention provides materials and methods allowing efficient and simple screening of several compounds in short periods of time. In particular, the instant methods can be partially automated, thereby allowing efficient and simultaneous screening of large sets of compounds.

When the activity of the candidate compound(s) is unknown, the method allows the screening or identification of compounds exhibiting the selected property (e.g, metabolic activity). Alternatively, when the activity (or type of activity) of the candidate compound(s) is known or expected, the method can be used to further characterize said activity (in terms of specificity, efficacy, etc.) and/or to improve said activity, by assaying derivatives of said candidate compounds.

The present invention thus resides in methods and compositions for screening, identifying, characterizing or improving neuro-active compounds, i.e., compounds which are active on neuronal cell function(s). According to the present invention, neuro-active compounds include any compound having the ability to alter (e.g., restore or correct) one or several functions of a cell (more specifically a neuron), in particular, capable of altering at least one metabolic pathway or biological or functional property of a neuron. A biologically active compound of this invention is more preferably a compound which is capable of altering (e.g., restoring, correcting) the survival, development, growth, maturation, neutrotransmission, death or regeneration of a cultured neuron. As an example, a biologically active compound of this invention is a compound which is capable of restoring a normal phenotype to an injured neuron or of at least partially inhibiting the deleterious effect of an injury on a neuron. Depending on the situation, the active compound may be selected for its capacity to repress or to activate a cellular mechanism, for its capacity to stimulate or inhibit a metabolic pathway, to restore a biological property, to prevent cell death, etc.

A particular embodiment of this invention resides in a method of identifying compounds active on neuronal cell function, said method comprising:

culturing an isolated specific neuronal cell population in vitro submitting the neuronal population to condition(s) altering the (or a) function of the cells, contacting the treated cells with candidate compounds in parallel, observing (at the cell level) the function of the cells, and selecting the compounds which are active on restoring said function.

As will be further discussed in this application, the cells are preferably cultured in multi-well device, in particular microtiter plates. Also, the function of the cells is, in a typical embodiment, observed (or assessed) in an automated fashion.

The present invention is particularly suited for screening (or identifying, characterizing or improving) compounds which are active on neuronal survival or development, more preferably which improve the survival and/or development of neurons.

Accordingly, in a particular embodiment, the invention resides in methods of identifying compounds that promote neuronal cell survival or development.

The present invention is also particularly suited for screening (or identifying, characterizing or improving) compounds which prevent programmed cell death of neurons. In this regard, preventing can be partial or complete. Preferred selected compounds are able to reduce (or delay) by at least 50% programmed cell death of neurons, as compared to untreated neurons.

One major advantage of the current invention resides in the use of isolated neuronal cell populations, i.e., essentially pure type-specific neuronal cultures. Indeed, the present invention now describes the purification of several specific neuronal cell populations, and demonstrates that said cell populations can be maintained in culture without losing their phenotype and function, and used for screening purposes. The invention further demonstrates that such specific neuronal populations can be submitted to various condition(s) and/or treatment(s) to alter their metabolic pathways or to induce pathological situation. The invention is particularly advantageous in that the use of specific neuronal populations allows a predictive and reliable assessment of the biological activity of a compound.

Various purified neuronal cell populations can be used in the present invention, including essentially pure cultures of motor neurons, forebrain cholinergic neurons, hippocampal neurons, dopaminergic neurons, gabaergic neurons, serotoninergic neurons, cerebellar granule cells, cortical neurons, striatal neurons, retinal ganglion cells. Preferred neurons to be used in the current invention include motor neurons. Indeed, these neurons are affected in motor neuron diseases or in specific neuro-degenerative diseases and provide very predictive information regarding the activity of compounds. Compounds with activity on said neurons represent candidate drugs for treating motor neuron diseases, including ALS, or potential leads for use in lead optimisation processes, in order to obtain such drugs. Other preferred neurons are neurons isolated from foetal sources, for example forebrain cholinergic neurons from the fore-brain (which can be used to select compounds active in Alzheimer disease), hippocampal neurons (Alzheimer's) and dopaminergic neurons (which can be used to select compounds active in Huntington's disease, Parkinson's disease and cerebral ischemia).

The isolated neurons used in the present invention may be of various origins, including mammalian origin (such as rodents, human beings, primates, etc.), chicken, etc. These isolated neuronal populations can be prepared according to particular methods which will be described below.

In a particular embodiment, the present invention comprises contacting several candidate compounds in parallel with the isolated neuronal cell population. As indicated above, the current invention is particularly suited for parallel (optionally simultaneous) testing of several different candidate compounds. Indeed, about one million neurons can be produced from one brain (or foetal litter), which allows the performance of roughly 10 000 screening assays. In a preferred embodiment, 1 to 1000 different candidate compounds are tested in parallel, more generally 1 to 500, even more preferably 1 to 100. In a typical experiment, the purified neurons are distributed into separate devices (for instance into different wells of a plate), and 1 to 100 compounds are screened simultaneously for their neuroactivity.

Furthermore, in an other particular embodiment, the present invention comprises contacting the candidate compound(s) in parallel with several different isolated neuronal cell populations. This embodiment is particularly advantageous since it allows the determination of the selectivity of the compounds, or their activity profile towards several different classes of isolated neurons. The invention thus also encompasses the use, in parallel, of several populations of isolated neurons, in order to determine the selectivity of a candidate compound. This aspect is particularly advantageous for selecting compounds active with respect to specific neuronal cell population(s), and inactive or essentially inactive with regard to other neuronal cell populations. In this regard, it has been described that caspase-3 inactivation prevents death of neurons in the brain, but not of motor neurons. Also, jnk1/jnk2 double knock-out mice exhibit a reduced programmed cell death in hindbrain and an increased programmed cell death in forebrain, further illustrating the selectivity of certain metabolic pathways in modulating neuronal activity. By providing isolated neuronal cell populations, the present invention now allows the screening of compounds which can affect the function (e.g., prevent programmed cell death) of certain types of neurons, without affecting the function of other types of neurons.

A preferred method of this invention therefore comprises contacting one or several candidate compounds in parallel with:
- at least two different isolated neuronal cell populations, and determining the effect of said candidate compounds on the function of said cells.

Preferably, 2 to 5 different neuronal cell populations are being tested in parallel, more preferably 2 to 3. In typical embodiments, at least two, preferably three different neuronal cell populations selected from motor neurons, cholinergic neurons and hippocampal neurons are tested in parallel. The term "in parallel" indicates that the compound(s) are tested separately on the different populations, preferably essentially at the same time.

In addition, other cell populations can be tested in parallel, including non-neuronal cell populations, in order to further evaluate the selectivity and/or the toxicity of a test compound.

In this regard, a further object of this invention resides in a method of identifying, selecting or characterizing a compound active on neuronal cell function, comprising contacting one or several candidate compounds in parallel with:
- at least one, preferably at least two different isolated neuronal cell populations, and
- at least one non-neuronal cell population, and determining the effect of said candidate compounds on the function of said cells.

Preferred non-neuronal cell populations include for instance haematopoietic cells (such as for instance T lymphocytes, B lymphocytes, macrophages, dendritic cells and progenitors thereof), intestinal tissue, hepatic cells, etc. In a preferred embodiment, at least haematopoietic cells are being used, which provide information regarding the selectivity and potential toxicity of the compounds. The non-neuronal cells may be primary cell cultures, in particular of human origin, or cell lines derived therefrom. The non-neuronal cells and the neuronal cells may be autologous, allogenic or xenogenic. In a particular embodiment, the neuronal cells are of murine origin and the non-neuronal cells are of human origin.

In this regard, the invention also lies in a method of profiling or assessing the toxicity potential of a candidate compound, comprising contacting in parallel said compound with an isolated neuronal cell population, and at least one non-neuronal cell population, preferably a human cell population selected from haematopoietic cells, intestinal tissue and hepatic cells.

The invention also resides in a method of identifying or selecting compounds that prevent programmed cell death of neurons, comprising contacting a test compound in parallel with:
- an isolated neuronal cell population, and
- a non-neuronal cell population, preferably a hematopoietic cell population, more preferably a population of T lymphocytes, and selecting the compound which prevents programmed cell death of neurons and essentially does not prevent programmed cell death of the non-neuronal cell population.

More generally, the present invention allows the screening of compounds which selectively affect the metabolism (e.g., the survival, development, etc.) of neurons, without affecting the metabolism of other neuronal and/or non-neuronal cell populations.

In a specific embodiment, the invention relates to a method for identifying compounds active on neuronal survival or neuronal development, comprising:
- purifying a specific neuronal population
- culturing the specific neuronal population in vitro
- submitting the neuronal population to condition(s) altering the capacity of the cells to grow or survive
- contacting the treated cells with candidate compounds in parallel,
- observing (at the cell level) the growth or survival of the cells, and
- selecting the compounds which are active on neuronal survival or development.

The methods of this invention can be performed in several ways. Generally, the method comprises providing isolated neuronal cell population(s), submitting the population(s) to condition(s) and/or treatment(s) that affect the metabolism of the cells, contacting the cells with the candidate compound(s) and determining the neuro-activity of said candidate compounds.

Provision of Isolated Neuronal Populations

Isolated, specific neuronal populations according to the present invention can be produced from various mammalian species, using various starting biological material. In particular, the isolated neurons can be prepared from different tissues including brain areas, spinal cord, ganglia, and the like, at various developmental stages. Preferably, however, the neurons are prepared from immature (e.g., foetal) tissues, which allow the production of viable neuronal cultures.

Preferred sources of neurons include rodents (in particular mouse and rat). Alternatively, the neuronal populations may be prepared from chicken or other animal species.

The biological material (nervous tissue) may also be obtained from previously modified animals (including transgenic animals), pathological animals or animals modified to facilitate investigations, for example "tagged" for the purification of specific neurons. As sources of neurons, it is advantageous to use a transgenic animal in which a membrane protein normally absent on neurons is expressed under the control of a neuron-specific promoter, for example the DOPA decarboxylase promoter. The tagged neurons (e.g., the dopaminergic neurons) can then be easily purified using an antibody to said protein.

A particular object of the present invention resides in an essentially pure culture of isolated hippocampal neurons. Another specific object of this invention is an essentially pure culture of isolated forebrain cholinergic neurons. Preferably, the above cultures are low cell density cultures, more preferably containing less that about 100 neurons/mm$^2$, even more preferably less than about 50 neurons/mm$^2$. Preferred embodiments of the present invention use neuron cultures at cell density below about 25 neurons per mm$^2$, preferably below 15 neurons per mm$^2$, even more preferably below 10 neurons per mm$^2$. As indicated below, the invention now proposes to screen compounds using low density neuron cell cultures, allowing an individual cell analysis to be performed, lower costs, a higher number of experiments from one single preparation, and a more relevant biological response to be measured.

In a specific embodiment, the isolated purified neurons of this invention are produced from a genetically modified animal, more preferably from an animal genetically modified to express a marker molecule on specific neuronal populations.

In order to produce isolated neuronal populations or cultures, the biological material collected is generally treated by dissection, mechanical treatment and/or enzymatic digestion, in order to dissociate the cells. The cells may then be separated by centrifugation and/or cell sorting (including immunomagnetic sorting). Centrifugation is preferably performed as gradient centrifugation, for instance in metrizamide. Where the nervous tissue has been obtained from genetically modified animals as described above, immunomagnetic sorting can be performed based on the specific markers expressed by the specific neuronal populations.

In a preferred embodiment, the isolated neuronal cell populations are produced from foetal nervous tissue. In a particular method, the isolated neuronal cell populations are produced by mechanical and/or chemical and/or enzymatic treatment of foetal nervous tissue. The invention indeed shows that functional, viable neuronal cell populations may be obtained from nervous tissues at certain stages of maturation.

Generally, starting from one litter of animals (e.g., a rodent), up to 1 million isolated neurons of several types can be produced, allowing about 50 000 tests to be performed. In a particular embodiment, several different neuronal cell populations are produced from one foetal rodent, which are being used in parallel screening assays according to this invention.

The isolated purified neurons may be maintained in culture in vitro in various culture medium suitable for mammalian cells, including Neurobasal or L15 media (Life Technologies, Rockville, Md.), which can be supplemented with various compounds including antibiotics, vitamins, trophic factors, foetal serum, etc. Preferably, the cells are cultured in Neurobasal medium, supplemented with nutrients and growth factors. The cells can be maintained for several days or weeks without losing their properties. Preferably, they are used shortly after production, i.e., preferably within a week after production.

More preferably, the invention now shows that isolated neurons can be cultured at low cell density, which facilitates industrial screening according to the present invention. Low density cell cultures of this invention contain more preferably less than about 100 neurons per mm$^2$, more preferably less than about 50 neurons per mm$^2$, even more preferably less than about 25 neurons per mm$^2$, even more preferably less than about 10 neurons per mm$^2$. The neuronal cell populations are preferably cultured in vitro in microtiter plates, preferably containing 384 wells or more. The invention shows that from one litter of animals, low cell density cultures can be prepared and distributed into microtiter plates, in particular microtiter plates with more than 384 wells, thereby allowing efficient and rapid screening of compounds.

Treatment of the Neurons

In the screening assays of this invention, the neurons are generally submitted to conditions and/or treatments that provoke disregulation, comparable to those encountered in pathological conditions. Preferably, the neurons are submitted to conditions and/or treatments that alter their function, more specifically their survival or development (e.g., growth). These include chemical, physical, genetic and/or enzymatic treatments, as well as culture specific culture conditions (temperature, environment, etc.).

Specific treatments or conditions include culture in the presence of death inducers, apoptosis (i.e., programmed cell death) inducers, glutamate agonists, stimulation of Fas and other pro-apoptotic receptors, trophic factor deprivation, etc.

Preferred death inducer treatments or conditions include:

Trophic deprivation: Growing cells in the absence of neurotrophic factors, which leads to rapid neuronal cell death. Trophic factors are for instance CNTF (Sendtner et al. (1992) Nature 358, 502–4), BDNF, or GDNF (Henderson et al. (1994) Science 266, 1062–1064). Trophic deprivation is illustrated for instance in example 4-compare Neurobasal to BDNF).

Glutamate toxicity: Domoic acid is a glutamate receptor agonist which does not cause down-regulation of glutamate receptors (as does glutamate itself). Domoic acid at $10^{-5}$M leads to loss of more than 50% of motor neurons after 24 hours (see is example), with even more dramatic effects after longer incubations.

Aβ peptides: Amyloid β-peptides are deposited in the brains of patients with Alzheimer's disease and are known to be toxic to differentiated hippocampal neurons in culture (e.g. Yankner et al.(1990) Science 250, 279–282). This is a very well established (and well studied) in vitro model of cell death related to Alzheimer's disease.

Another preferred way to alter neurons is to transfect neurons with nucleic acid sequences that mimic human disease process(es). A preferred vector is a recombinant lentiviral vector (i.e., a recombinant nucleic acid or sequence incorporated into a reconstituted lentiviral particle).

Another preferred way to alter neurons is to introduce chemical(s) or peptide(s) in the cytoplasm, using for instance peptide vectors. A preferred vector is penetratin.

These various conditions and treatments can be used separately or in combinations, and may be selected by those skilled in the art depending on the selected profile of the compounds.

In preferred embodiment, where compounds that promote neuronal survival or development are sought, treatments comprise preferably trophic deprivation, glutamate toxicity or apoptosis-inducers.

In another preferred embodiment, where compounds that prevent programmed cell death of neurons are sought, the treatment comprises preferably the contact with apoptosis-inducers or trophic factor deprivation.

Contacting Cells with the Compounds

The screening methods of this invention comprise a step of contacting the candidate compounds with the selected isolated neuronal cell population(s). The compounds may be contacted for various periods of time, depending on their effect, concentration, the neuronal population, and/or the evaluation technique.

Generally, the cells are exposed to candidate compound(s) in the range from 1 nM to 1 mM. It should be understood that other concentrations may be tested without deviating from the instant application. Furthermore, each compound may be tested, in parallel, at several concentrations.

Furthermore, if necessary, different adjuvants and/or vectors and/or products helping the compounds to penetrate the cells may be added, including liposomes, cationic lipids or polymers, penetratin, Tat PDT, peptides from adenoviruses (e.g., penton or fiber) or other viruses, etc.

Contacting can be performed in any appropriate support or device, including plate, tube, flask, and the like. Generally, contacting is performed in multi-well plates, allowing multiple assays to be carried out in parallel. Typical supports include microtiter plates, especially the 384-well microtiter plate format, which is easy to manage and easy to illuminate with conventional excitation.

Preferably, about 10 to 200 isolated neurons are used for each screening point, in any suitable culture medium as described above. In this regard, a particular aspect and advantage of the method according to this invention lies in the use of low numbers of neurons and/or neurons cultured at low cell density. Indeed, by using low cell density neuron cultures, it is possible to perform very high numbers of tests from one single preparation, allowing higher reproducibility and more economic tests. But more importantly, the use of such low density neuron cell cultures provides a more relevant biological response. Indeed, it has been reported that neurons produce their own survival factors so that, at high density, neurons exhibit a particular pattern of reaction to stimuli, and show increased resistance to apoptosis or trophic factor privation, for instance. The use of low density cell populations thus facilitates the pre-treatment or conditioning of the neurons. In addition, using low density neuron cell cultures according to this invention allows an individual cell analysis to be performed (i.e., an observation at the cell level). In this regard, it is now possible to monitor the activity of a test compound by analysing each cell individually (or some of the cells in the culture individually), so as to obtain a precise and reliable response.

Preferably, the above low cell density cultures contain less that about 100 neurons/mm$^2$, even more preferably less than about 50 neurons/mm$^2$. Preferred embodiments of the present invention use neuron cultures at cell density below about 25 neurons per mm$^2$, preferably below 15 neurons per mm$^2$, even more preferably below 10 neurons per mm$^2$.

Activity of the Compounds—Screening

Determining the neuro-active profile of the candidate compounds can be performed according to several methods. In particular, different end points may be measured, in order to assess the neuro-activity of the compounds, such as: survival, expression of antigens, transcription of specific genes, morphological changes—size, neurite growth, etc.

The tests for activity on neurons are preferably:

The calcein assay for testing survival,

Morphometric analysis, such as neurite length and/or branching, which can be carried out on fixed neurons using commercially available programs, and Immunolabelling of antigens.

Preferably, the neuro-activity of the candidate compounds is determined by comparison with control neuronal cell populations, in the absence of any compound and/or treated with reference compounds.

In a more particular embodiment, the activity of the candidate compounds is determined by comparing the survival of the purified neurons in the absence of the candidate compound with the survival in the presence of the candidate compound over the same time period.

In another particular embodiment, the activity of candidate compounds is determined by comparing the expression of a cellular antigen in the purified neurons in the absence of the candidate compound with the expression of said cellular antigen in the presence of the candidate compound over the same time period.

Determining the status of the neurons can be performed by evaluating different physical measurements, optical properties, fluorescence at various wavelengths, luminescence etc. Different instruments may be used, including plate readers, automated microscopes, fitted with lamps or lasers, etc. Other techniques include light detection through refrigerated CCD camera. The signals measured may be treated according to known techniques, using for instance software including pixel histogram, cluster analysis and morphology analysis. In a preferred embodiment, the cell population is analysed at the cell level, i.e., cell by cell individually. In this regard, it is now possible to monitor the activity of a test compound by analysing each cell individually (or some of the cells in the culture individually), so as to obtain a precise and reliable response. This is in clear contrast with previous methods, based on the monitoring of the cell population as a whole, and not on a cell by cell basis. The method of this invention thus allows to determine the activity of a test compound by observing or monitoring each (or some) individual cells the cell population. Such a determination allows higher specific signal to be obtained, reduce the non-specific, background signal, is more informative, etc.

As indicated above, the invention now allows the rapid and reliable screening, in parallel, of large numbers of candidate compounds on one or several isolated neuronal cell populations. The methods are predictive, automated and suitable for screening, profiling or improving any type of compound, and may be used to identify candidate neuro-active drugs for treating neuro-degenerative disorders.

In this regard, the invention also concerns kits for use in assessing the neuro-activity of a candidate compound, comprising an isolated neuronal cell population, a support and, optionally, means to induce metabolic alteration(s) to the neurons and/or means to assess any metabolic change in a neuronal population.

The invention also encompasses the use of any compound (or derivatives thereof) identified, selected, profiled or characterized by the above disclosed methods, (i) as targets for experimental research or (ii) for the manufacture of pharmaceutical compositions for treating neurological disorders.

Other aspects and advantages of the instant invention will be disclosed in the following experimental section, which should be regarded as illustrative and not limiting the scope of the present application.

LEGEND TO THE FIGURES

FIG. 1: Determination of isolated motor neuron survival following trophic deprivation and treatment with sodium valproate (A) or (4-carboxyphenyloxyamino) butanoic acid (B).

Figure 2:
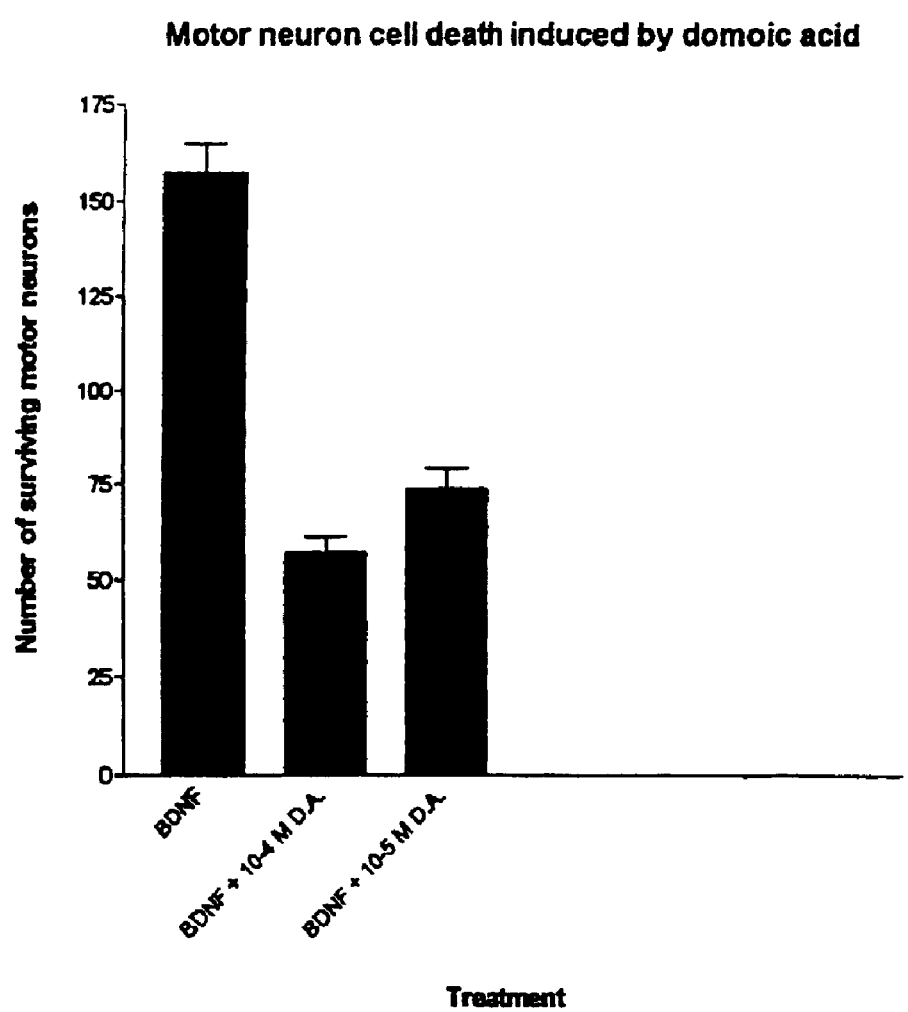

FIG. 2: Induction of motor neuron cell death by treatment with various concentrations of domoic acid.

FIG. 3: Observation of wells containing neurons in low density culture, following treatment with test compound.

EXAMPLES

Example 1

Purification of Rat Motor Neurons

Spinal cords are dissected from day E14.5 sprague Dawley rat embryos (Camu et al., (1993) In: "Immunoselection Strategies for Neural Cell Culture", Neuroprotocols: A companion to Methods in Neurosciences 2, 191–199). The dorsal part of the spinal cord is cut away, and the meninges removed. Each cord is cut into pieces using a scalpel and placed into 1 ml modified F10 medium (Ca2+, Mg2+-free, no glutamine or phenol red), with 0.025% trypsin, at 37° C. for 10 minutes. The fragments are transferred to 1 ml L15 containing 0.4% BSA and 0.1 mg/ml Dnase, and triturated using a blue (1 ml) tip. Cells are then spun through a BSA (4% w/v) cushion for 5 minutes at 480 g. The small cells are removed using a metrizamide (Serva) density gradient: 6.5% (w/v) metrizamide is placed under the cell suspension and centrifuged for 15 minutes at 860 g. The large motor neurons stay at the interface between the medium and the metrizamide, while the small cells (including non-neuronal cells) are pelleted. The cells at the interface are collected, washed, then further purified using magnetic cell sorting. Cells are incubated with primary the antibody (anti-rat p75 antibody [192]) 0.5% BSA in PBS, washed and incubated with microbeads coated with a goat anti-mouse secondary antibody. After 15 minutes at 4° C., the cells are washed again and the antibody-bound cells separated using a strong magnetic field.

Cells are centrifuged through a BSA cushion and resuspended in neurobasal medium supplemented with B27 (Life Technologies), 2% horse serum, 0.5 mM glutamine, 25 µM 2-mercaptoethanol, 25 µM glutamate. Cells are plated onto dishes coated with polyornithine and laminin (both at 3 µg/ml).

Example 2
Purification of Rat Hippocampal Neurons

This method is based on a modification of the classical hippocampal cultures (Goslin & Banker (1990) In "Culturing nerve cells" (G. Banker & K. Goslin, Eds), pp251–281. MIT Press, Cambridge), but using the metrizamide gradients (as above) to remove non-neuronal cells and small neurons.

Hippocampi from 10–12 rat embryos (E18) are dissected in HBSS+ (Ca2+/Mg2+-free HBSS, 7 mM HEPES, 4.5 g/L glucose). Tissue is trypsinized in 0.25% trypsin for 15 minutes at room temperature, washed three times with HBSS+, then triturated with glass Pasteur pipettes. Cells are then spun through a BSA (4% w/v) cushion for 5 minutes at 480 g. The small cells are removed using a metrizamide (Serva) density gradient: 6.5% (w/v) metrizamide is placed under the cell suspension and centrifuged for 15 minutes at 860 g. The neurons stay at the interface between the medium and the metrizamide, while the small cells (including non-neuronal cells) are pelleted. The interface is collected and the cells spun through a BSA cushion. Cells are plated onto poly-ornithine/laminin-coated coverslips and grown at 37° C., 5% CO2 in Neurobasal medium supplemented with B27, 2% horse serum, 0.2 mM glutamine, 1 mM pyruvate.

Example 3
Purification of Septal Cholinergic Neurons

Septa from 10–12 rat embryos (E17) are dissected in HBSS+ (Ca2+/Mg2+-free HBSS, 7 mM HEPES, 4.5 g/L glucose). Tissue is trypsinized in 0.25% trypsin for 15 minutes at room temperature, washed three times with HBSS+, then triturated with glass Pasteur pipettes. Cells are then spun through a BSA (4% w/v) cushion for 5 minutes at 480 g. The small cells are removed using a metrizamide (Serva) density gradient: 6.5% (w/v) metrizamide is placed under the cell suspension and centrifuged for 15 minutes at 860 g. The large neurons stay at the interface between the medium and the metrizamide, while the small cells (including non-neuronal cells) are pelleted. The cells at the interface are collected, washed, then further purified using magnetic cell sorting. Cells are incubated with primary the antibody diluted in 0.5% BSA in PBS, washed and incubated with microbeads coated with a secondary antibody. After, for 15 minutes at 4° C., the cells are washed again and the antibody-bound cells separated using a strong magnetic field. Cells are plated onto poly-ornithine/laminin-coated coverslips and grown at 37° C., 5% CO2 in neurobasal medium supplemented with B27, 2% horse serum, 0.2 mM glutamine, 1 mM pyruvate and NGF (50 ng/ml).

Example 4
Induction of Cell Death on Motor Neurons and Analysis of Survival

Rat motor neurons were isolated and purified as described in example 1 and cultured for 3 days in Neurobasal medium without neurotrophic factors (i.e. trophic factor withdrawal) in 4-well plates in the presence or absence of the test molecule. The neurotrophic factor BDNF is used as a positive control for all experiments. FIG. 1A shows an example of a small molecule (sodium valproate) that enhances survival of motor neurons on trophic factor withdrawal. FIG. 1B shows an example is of a small molecule that has no effect on motor neuron survival. FIG. 2 shows the induction of motor neuron cell death by glutamate toxicity. Motor neurons were grown for 3 days in vitro, then domoic acid at various concentrations was added and the number of surviving motor neurons was counted after 26 hours.

The survival can also be followed using Calcein labelling: Cells are treated with a final concentration of 4 µM Calcein-AM (Molecular Probes) in medium, and incubated at 37° C. for 30 minutes. The medium is removed, the cells rinsed with 20% glycerol in L15 (without phenol red) and cells were analysed by counting the number of fluorescent cells.

Figure 3A:
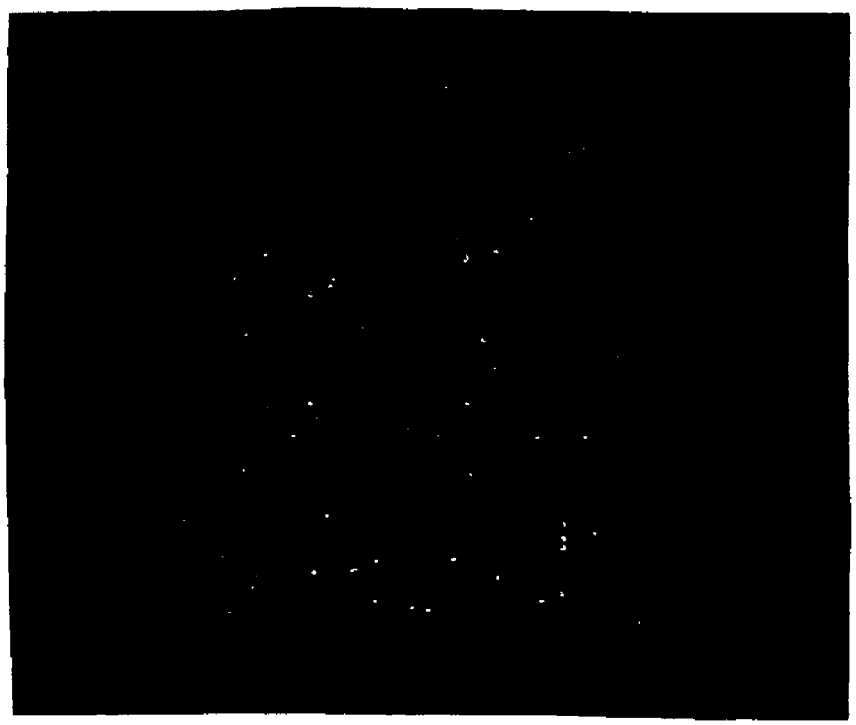
Figure 3B:
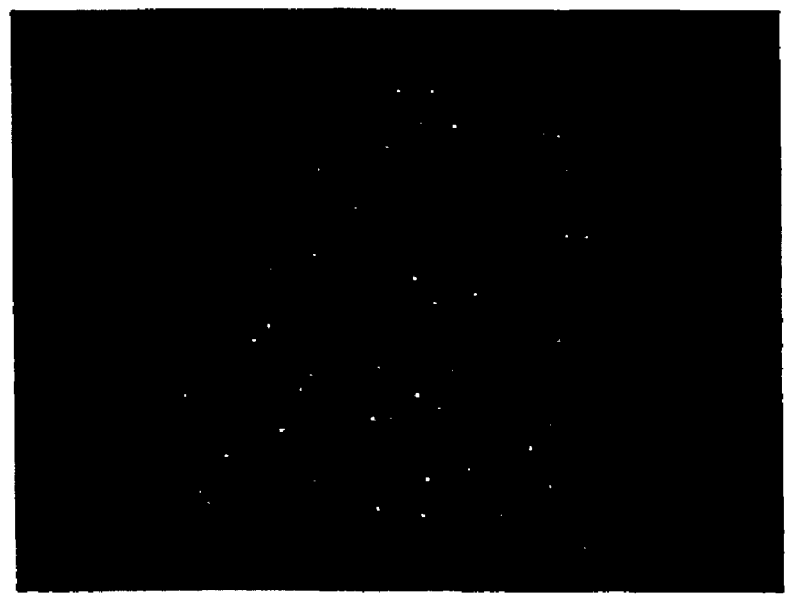

FIG. 3 represents two 9 mm$^2$-wells of a microtitration plate (384 wells) containing low-density cultures of isolated neurons according to this invention. The cultures were subjected to growth factor privation to induce apoptosis, and treated or not with BDNF. As shown in FIG. 3A, treatment with BDNF effectively protects the neurons (73 neurons are present, which can be observed and/or monitored individually), while in the absence of active compound, 18 neurons are present only (FIG. 3B). The exclusion threshold is below 300 µm$^2$. These results further illustrate the ability of the invention to use low-density cultures of isolated, specific neurons, to analyse test compounds on a high throughput basis, by individual cell monitoring.

What is claimed is:

1. A method for screening for neuro-active compounds, said method comprising:

purifying sufficient quantities of motor neurons or striatal neurons from animal nervous tissue, culturing the purified neurons in vitro in a microtiter plate at a cell density of 50 neurons/mm$^2$ or less, submitting the purified neurons to chemical, physical or enzymatic treatment altering the capacity of the cells to grow or survive, contacting cultures of the treated cells in parallel with several different candidate compounds, quantifying the growth or survival of the neurons, and selecting the compounds which are active on survival or growth, said compounds being neuro-active.

2. The method of claim 1, wherein the purified neurons are of rodent origin.

3. The method of claim 2, wherein the neurons are purified from a wild-type, transgenic, pathological or modified mouse.

4. The method of claim 1, wherein the purified neurons are of human origin.

5. The method of claim 1, wherein the cultured neurons are exposed to candidate compounds in the range from 1 nM to 1 mM.

6. The method of claim 1, wherein the neurons are cultured in a microtiter plate containing 384 wells or more.

7. The method of claim 1, wherein the cultured neurons are contacted in parallel with up to 1000 different candidate compounds.

8. The method of claim 1, wherein the activity of the candidate compounds is determined by comparing the survival of said purified neurons in the absence of the candidate compounds with the survival in the presence of the candidate compounds over the same time period.

9. The method of claim 1, wherein the neurons are prepared from immature tissue.

10. The method of claim 1 for identifying, selecting or characterising a compound that prevents programmed cell death of neurons and does not prevent programmed cell death of a non-neuronal cell population, said method further comprising a step of contacting the selected candidate compounds with a non-neuronal cell population and selecting compounds that do not prevent programmed cell death of said cell population.

11. A method for screening for compounds active on motor-neuron survival or growth, said method comprising:

purifying sufficient quantities of motor-neurons from a non-transgenic non human mammal, culturing the purified neurons in vitro in a microtiter plate at a cell density of 50 neurons/mm$^2$ or less, submitting the purified neurons to a chemical treatment altering the capacity of the cells to grow or survive, contacting cultures of the treated cells in parallel with up to 1000 different candidate compounds, quantifying the growth or survival of the neurons, and selecting the compounds which are active on survival or growth.

12. The method of claim 1, wherein the purified neurons are cultured in vitro in a microtiter plate at a cell density of 25 neurons/mm$^2$ or less.

* * * * *